United States Patent [19]

Phillipps et al.

[11] 4,016,271

[45] Apr. 5, 1977

[54] 21-ADAMANTANE-1'-CARBOXYLATE STEROID COMPOSITIONS

[75] Inventors: Gordon Hanley Phillipps, Wembley; Alan Frederick English, Hazlemere; Gillian Helen Stribley, Northwood, all of England

[73] Assignee: Glaxo Laboratories Limited, Greenford, England

[22] Filed: Nov. 19, 1975

[21] Appl. No.: 633,178

Related U.S. Application Data

[63] Continuation of Ser. No. 429,793, Jan. 2, 1974, abandoned.

[30] Foreign Application Priority Data

Jan. 3, 1973 United Kingdom ............... 447/73
Jan. 3, 1973 United Kingdom ............... 448/73

[52] U.S. Cl. .............................................. 424/243
[51] Int. Cl.² ....................................... A61K 31/56
[58] Field of Search ............... 424/243; 260/397.45

[56] References Cited

UNITED STATES PATENTS 3,857,941  12/1974  Ercoli et al. ................... 260/397.45

FOREIGN PATENTS OR APPLICATIONS 1,056,198  3/1976  United Kingdom .......... 260/397.45

*Primary Examiner*—Elbert L. Roberts
*Attorney, Agent, or Firm*—Bacon & Thomas

[57] ABSTRACT

The Specification describes a method of systemically treating immunological disorders or inflammatory disorders having a significant immunological component which comprises administering to a subject suffering from such a disorder an initial dosage in the case of a human adult subject of 50 to 500 mg of from more than betamethasone 21-adamantane-1'-carboxylate, dexamethasone 21-adamantane-1'-carboxylate or a corresponding 11-ketone, or in the case of other subjects, an equivalent dosage calculated on the body weight of the subject. The Specification further describes pharmaceutical and veterinary compositions for use in the above method, each dosage unit containing 50 to 500 mg of the 21-adamantane-1'-carboxylate steroid.

9 Claims, No Drawings

21-ADAMANTANE-1'-CARBOXYLATE STEROID COMPOSITIONS

This is a continuation, of application Ser. No. 429,793, filed Jan. 2, 1974 now abandoned.

The present invention is concerned with improvements in or relating to the medicinal use of betamethasone 21-adamantane -1'-carboxylate, its 16α-methyl analogue, and the corresponding 11-ketones, as more particularly described hereinafter.

Belgian Specification No. 785812 describes and claims betamethasone 21-adamantane- 1'-carboxylate and its corresponding 9α-chloro analogue, these compounds being described in our said Application as having prolonged antiinflammatory activity upon internal administration. As indicated in our Application, the above-mentioned compounds may advantageously be administered at intervals of several days in view of their prolonged duration of activity, an interval of 14 days being mentioned for intramuscular and intraarticular administration of the compounds to humans and an interval of 7–21 days for administration to animals. Our said Specification further describes dosages at which the compounds may be administered over such intervals to achieve a satisfactory antiinflammatory effect. Thus, for intramuscular administration to adult humans a dosage rate of 5–40 mg, preferably 10–20 mg of steroid is recommended, while for intra-articular administration the recommended dosage is 1–20 mg, preferably 3–6 mg of steroid. For animals, a recommended dose rate is 0.1 to 0.5 mg steroid per kg animal weight. Dosage units are described containing 1–50 mg of steroid.

We have now discovered that in treating inflammatory disorders associated with a significant immunological component, very valuable long-lasting therapeutic effects can be achieved by the administration of betamethasone 21-adamantane-1'-carboxylate, its 16α-methyl analogue and the corresponding 11-ketones in initial doses larger than those hitherto proposed in our said Application. The 21-adamantane-1'-carboxylates of betamethasone and dexamethasone are particularly preferred, the betamethasone compound being especially advantageous.

The present invention is thus concerned with the use in human and veterinary medicine of high dose levels of the 21-adamantane-1'-carboxylates of betamethasone, dexamethasone, 11-dehydrobetamethasone and 11-dehydrodexamethasone.

For example, by the use of such large initial doses of the active steroid in treating such disorders, it is possible to obtain a systemic effect having a far longer duration of action than would have been expected solely from the increase in the amount of the compound employed. Indeed, the duration of the effect has been found to be significantly greater than that of any comparable steroid. For example, the active steroids according to the present invention can, in certain cases, provide relief from such inflammatory disorders having a high immunological component for periods of up to 4–8 weeks or even longer using a suitable initial dose of the steroid, as more particularly described hereinafter, whereas steriods such as betamethasone are not observed to give relief for prolonged periods after administration and in some cases symptoms recur rapidly and may be at an increased level.

We have further discovered that the use of large doses of the active steroids provides an unusually valuable immunosuppressive effect. Experiments have shown that there appears to be arrest of the pathological immune response whilst normal immunological competence recovers. Thus, the steroids can generally be employed for the treatment of disorders having an immunological basis, e.g. for the suppression of harmful immunological reactions.

It is further observed from experiments on rats that blood 11-hydroxy corticosteroid levels are lowered for only a relatively short period of time whereas the anti-inflammatory and/or immunosuppressive effects appear to persist for longer periods of time.

In the systemic treatment of immunological disorders or inflammatory disorders having a significant immunological component, the initial dosage in the human adult (average weight 70 kg) is above 50 mg, advantageously being, however, not greater than 500 mg. A suggested initial dose of betamethasone 21-adamantane-1'-carboxylate is about 100–200 mg.

Betamethasone and dexamethasone are usually administered systemically for treating inflammatory conditions in man, in rather low doses for example, about 2 mg. Our above copending application describes dosage units containing up to 50 mg betamethasone 21-adamantane-1'-carboxylate.

In order to take advantage of the present finding that high initial doses of the adamantoates are exceptionally beneficial, it is more convenient to formulate them in dosage units containing more than 50 mg active steroid and it will be appreciated that dosage units containing such large quantities of corticoids represent a radical departure from previous practice.

According to a further feature of the invention, therefore, we provide pharmaceutical and veterinary compositions in dosage unit form, each dosage unit containing from more than 50 mg to 500 mg, preferably from more than 50 to 200 mg, of betamethasone 21-adamantane-1'-carboxylate, dexamethasone 21-adamantane-1'-carboxylate or a corresponding 11-ketone.

The initial dosage of steroid given both to human adults and children and to animals can best be expressed on a mg/kg basis. Thus, the dosage range of from more than 50 to 500 mg given above for a 70 kg human adult may be represented as the range 0.7 to 7.1 mg/kg. Although those dosages will also be affected by the surface area when considering children and animals, the dosages will still fall within the above range. A preferred dosage range is 1 to 5 mg/kg for humans and 3 to 7 mg/kg in animals.

In order to achieve the desired therapeutic effect, the above-defined initial dosage may be given on a single day or may be divided into separate doses given over a period of not more than 7 days, for example at 1–3 day intervals. The dosage regime may thus, for example, comprise three administrations of the steroid over three days or two administrations over two or three days, the total dosage over this initial period being within the limits set out above.

It will be appreciated that the precise initial dosage and the number and frequency of separate divided dosages will generally depend inter alia upon the nature of the disorder being treated, its severity, the precise route of administration of the steroid and the condition, age and weight of the patient. It will be appreciated that allowances, e.g. based on body weight or surface area, should be made in calculating dosages for children.

The initial dosage of the steroid provides suppression of the disorder for an initial long period, e.g. for a period of 2–8 weeks or even longer. In some cases, particularly in the treatment of rheumatoid arthritis, the initial dosage of the steroid may result in a complete arrest of the disorder under treatment. Such arrest has not previously been thought feasible.

In severe cases, further administration of the steriod at a lower do age level, for example, 1/16 to 1/4 of the original dose e.g. 10–20 mg, may be required to maintain suppression of the disorder but this treatment may eventually be withdrawn without the recurrence of the disorder which is commonly observed in treatment with conventional corticosteroids.

The steroid compounds are advantageously administered by injection, preferably by the intramuscular route, although the subcutaneous, intravenous or intra-articular routes may be used if desired. The steriod compounds are thus conveniently presented in the form of injectable preparations adapted for administration of the steroid by such routes.

The above-mentioned pharmaceutical and veterinary compositions according to the present invention thus conveniently comprise betamethasone 21-adamantane-1'-carboxylate, dexamethasone 21-adamantane-1'-carboxylate or a corresponding 11-ketone. The compositions will normally include a pharmaceutical or veterinary carrier or excipient. Compositions adapted for parenteral administration, preferably by the intramuscular route, may for example be formulated in a sterile aqueous vehicle. The injectable compositions may be conveniently presented in sealed ampoules or vials containing an aqueous suspension of the active steriod formulated for example with the aid of conventional excipients such as dispersing agents, suspending agents, stabilising agents etc.

Alternatively, the steroids may be administered via the gastrointestinal tract e.g. in the form of orally acceptable preparations or in the form of suppositories. For oral administration, the pharmaceutical and veterinary compositions according to the invention may be formulated with aid of one or more appropriate pharmaceutical or veterinary carriers or excipients which may be solid or liquid. Such orally administrable compositions may be formulated for example as tablets, capsules, granules etc. For oral administration, the dosages of the steroid may be greater (for example up to 4 times greater) than those indicated above for administration of the compound by injection.

The use of the steriod compounds in the above described manner enables one to treat a wide variety of disorders which is general may be roughly classified as disorders associated with inflammatory conditions having a significantimmunological component and disorders arising from harmful immunological reactions.

The administration of the compounds in the above described manner will be particularly valuable for the treatment of rheumatoid arthritis since the initial dosage rapidly will bring the disorder under control, as indicated by a reduction in fever (if the disorder is severe), relief of pain and reduction in the swelling at the joints. Medical opinion considers that rheumatoid arthritis is a disease in which both immunological and inflammatory reactions play a part.

The immuno-suppressive component of the activity of the corticosteroids discussed herein can be demonstrated by their effects in treating experimental allergic encephalomyelitis in rats. This experimental condition which is known to have a considerable immunological component can be regarded as a model for multiple sclerosis in the human. Results have shown that the disorders can be treated successfully by the above method.

The method may be used in disorders where there is an inflammatory and/or immunological process causing damage to the tissues. Disorders where such a mechanism is believed to play a part in the pathogenesis are listed below.

In the literature some of these disorders have been referred to as "autoimmune" which in the strict sense of the word means an immune response by the patient to his own tissues. The initiating aetiological event may not itself have been autoimmune but may have been brought about by infectious or toxic agents. However, these agents directly or indirectly set up immunological processes which damage the tissues. For the present purposes such disorders are included.

The disorders which may be treated in accordance with the present invention include exfoliative dermatitis and severe pemphigus, severe systemic lupus erythematosis, status asthmaticus and severe asthma, complications arising from acute lymphatic leukaemia and other leukaemias, (such as haemolytic anaemia and thrombocytopenic purpura), acquired haemolytic anaemia, severe hypersensitivity reactions (e.g. serum sickness, angioneurotic oedema and trichiniasis), collagen diseases, rheumatic fever especially if there is cardiac involvement, chronic discoid lupus erythematosus, polyarteritis nodosa, scleroderma, polymyositis, dermatomyositis, giant-cell arteritis (especially if vision is affected), ankylosing spondylitis, ulcerative colitis, regional ileitis, sarcoidosis (especially if there is hypercalcaemia, pulmonary fibrosis or CNS involvement), blood diseases due to circulating antibodies, (e.g. haemolytic anaemias, thrombocytopenic purpura, agranulocytosis), eye diseases (such as Sjogrens syndrome), nephrotic syndromes, post-hepatic oirrhosis with fever and other autoimmune disorders such as Hashimoto's disease. The steriod compounds can also be employed in accordance with the invention to control or prevent transplant rejection.

The method of the present invention can, as indicated above, be used to treat veterinary disorders associated with inflammatory conditions having a significant immunological component and/or disorders caused by harmful immunological reactions. Such disorders include, for example:-

1. Chronic eczema in cats and dogs.
2. Inflammatory conditions of the lung (pneumonia) (especially in the bovine).
3. Inflammatory conditions of the bovine udder (mastitis).
4. Inflammatory conditions of the gastrointestinal tract (e.g. calf or piglet scours).
5. Muscle and joint conditions (rheumatic and arthritic).

The adamantoate steroids here concerned may be prepared, for example, as described in the following Preparations.

PREPARATION 1

Betamethasone 21-adamantane-1'-carboxylate

9α-Fluoro-11β,17-dihydroxy-21-iodo-16β-methyl-pregna-1,4-diene-3,20-dione (76.65g) was dissolved in warm acetone (400 ml) and then adamantane carboxylic acid (54 g) and triethylamine (52.5 ml) were added and washed in with more acetone (100 ml). The solution was refluxed for one hour and then poured with good stirring into cold water (2.5 l). Filtration of the precipitated material and recrystallisation from aqueous methanol with charcoaling afforded betamethasone 21-adamantane-1'-carboxylate showing extensive melting 245–250° (Kofler) with subsequent crystal formation in the melt followed by slow decomposition and melting at 297°–300°, $[\alpha]_D + 114°$ (c 1.4 dioxan), $\lambda_{max}$ (in EtOH) 238nm ($\epsilon$ 16,800).

PREPARATION 2

Dexamethasone 21-adamantane-1'-carboxylate.

A solution of dexamethasone (3 g) in dry tetrahydrofuran (100 ml) was treated with adamantane carbonyl chloride (7.6 g) in tetrahydrofuran (35 ml) and pyridine (7 ml) and the mixture refluxed for 5.5 hours. The cooled solution was filtered from solid material and evaporated in vacuo to small bulk. Dilution with dilute sodium bicarbonate solution afforded an oil which was extracted with ethyl acetate. The washed and dried extracts were evaporated in vacuo to yield the crude ester contaminated with adamantane carbonyl chloride. This solid was heated on a steam-bath in pyridine (36 ml) and water (6 ml) for 2.5 hours. Dilution with water gave the adamantane carboxylate which was crystallised twice from ethyl acetate to give dexamethasone 21-adamantane-1'-carboxylate m.p. 285°289° decomp., $[\alpha]_D$ +85° (c, 1.0, dioxan), $\lambda_{max}$ 239 nm ($\epsilon$ 15,540).

PREPARATION 3

11-Dehydrobetamethasone 21-adamantane-1'-carboxylate

A solution of betamethasone 21-adamantane-1'-carboxylate (0.3 g) in acetone (180 ml) was cooled and stirred in an ice-bath whilst Jones reagent (1.5ml; prepared by dissolving 66.7 g chromium trioxide in 53.3 ml concentrated sulphuric acid and making up to 250 ml with water) was added dropwise over a period of 10 minutes. Further portions of reagent (0.8 ml and 0.4 ml) were added after 20 minutes and 80 minutes. When the reaction was judged complete, the green chromium salts were removed by filtration and the mother liquors partially evaporated in vacuo. The resulting solution was diluted with water and extracted with ethyl acetate.

The washed and dried (MgSO$_4$) extracts were evaporated and the residue recrystallised twice from methanol to afford 11-dehydrobetamethasone 21-adamantane-1'-carboxylate, m.p. 241°–244° decomp., $[\alpha]_D +$ 149° (c 1.0 dioxan), $\lambda_{max}$ 236 nm (68 15,800).

The active steroids employed in accordance with the present invention may be administered in the form of the following injectable preparations.

EXAMPLE 1

| | | |
|---|---|---|
| Active steroid (particle size; < 100μ; 10–75% > 5μ) | 2.00% | w/v |
| Benzalkonium chloride (anhydrous equivalent) | 0.015 | " |
| Tween 80 (polyoxyethylene-(20) sorbitan mono-oleate). | 0.010 | " |
| Tween 81 | 0.005 | " |
| Hydroxyethylcellulose | 0.100 | " |
| Sodium dihydrogen phosphate (dihydrate) | 0.017 | " |
| Disodium hydrogen phosphate (anhydrous) | 0.043 | " |
| Sodium chloride | 0.710 | " |
| Benzyl alcohol | 1.00% | v/v |
| Water for injection | to 100.00 | |
| pH 6.0 – 7.0 | | |

PREPARATION OF INJECTABLE SUSPENSION

The sodium chloride and phosphates are mixed with the hydroxyethyl cellulose, dissolved in water, benzyl alcohol added and the solution then sieved or filtered and then sterilized by autoclaving to provide the vehicle for the suspension. The Tweens and benzalkonium chloride are together dissolved or dispersed in a small portion of the available water, mixed with the active steroid and the suspension is sterilized by autoclaving at 10 psi for 1 hour.

The sterile vehicle and the steroid suspension are then mixed aseptically and subjected to high shear stirring. The suspension is made up to volume with water, sieved, and filled into 3, 4, or 5 ml ampoules each containing 20 mg/ml of active steriod.

Similar preparations may be made in 1, 2, 3, 4 or 5 ml ampoules each containing 50 mg/ml of active steroid or 2, 3, 4 or 5 ml ampoules each containing 30 mg/ml active steroid.

EXAMPLE 2

Injectable Preparations containing betamethasone 21-adamantane-1'-carboxylate Composition

| | | |
|---|---|---|
| Betamethasone 21-adamantane-1'-carboxylate (sterile reprecipitated; particle size <100μ; 10–75% >5μ) | 2.00% | w/v |
| Benzalkonium chloride (anhydrous equivalent) | 0.015 | " |
| Tween 80 (polyoxyethylene-(20) sorbitan mono-oleate) | 0.010 | " |
| Tween 81 | 0.005 | w/v |
| Hydroxyethylcellulose | 0.100 | " |
| Sodium dihydrogen phosphate (dihydrate) | 0.017 | " |
| Disodium hydrogen phosphate (anhydrous) | 0.043 | " |
| Sodium chloride | 0.710 | " |
| Benzyl alcohol | 1.00% | v/v |
| Water for Injection | to 100.00 | |
| pH 6.0 – 7.0 | | |

PREPARATION OF THE REPRECIPITATED BETAMETHASONE 21-adamantane-1'-carboxylate 100 g of betamethasone 21-adamantane-1'-carboxylate are dissolved in a mixture of 1100 mls of dimethyl acetamide with 21.6 grams of Tween 80. This solution is added with stirring to 7.5 liters of 1% v/v aqueous solution of benzyl alcohol. The resulting suspension is centrifuged, the supernatant liquid removed and the suspended material washed with water and recentrifuged. The supernatant liquid is again removed and the suspension made up to 2.0 liters with water. The suspension is then sieved (200 mesh).

PREPARATION OF INJECTIBLE SUSPENSION

The sodium chloride and phosphates are mixed with the hydroxyethyl cellulose, dissolved in water, benzyl alcohol added and the solution then sieved or filtered and then sterilized by autoclaving to provide the vehicle for the suspension. The Tweens and benzalkonium chloride are together dissolved or dispersed in a small portion of the available water, mixed with the reprecipitated betamethasone 21-adamantane- 1'-carboxylate and the suspension is sterilized by autoclaving at 10 psi for 1 hour.

The sterile vehicle and the betamethasone 21-adamantane- 1'-carboxylate suspension are then mixed aseptically and subjected to high shear stirring. The suspension is made up to volume with water, sieved, and filled into 3, 4, or 5 ml ampoules each containing 20 mg/ml of betamethasone 21-adamantane- 1'-carboxylate.

Similar preparation may be made in 1,2,3,4 or 5ml ampoules each containing 50mg/ml of active steriod, or 2, 3, 4 or 5 ml ampoules each containing 30 mg/ml of active steriod.

We claim:

1. Pharmaceutical and veterinary compositions in dosage unit form for the systemic treatment of immunological disorders or inflammatory disorders having a significant immunological component, each dosage unit containing more than 50 mg but not more than 500 mg of betamethasone 21-adamantane- 1'-carboxylate, dexamethasone 21-adamantane- 1'-carboxylate or a corresponding 11-ketone , and a pharmaceutical or veterinary carrier or excipient.

2. Compositions as defined in claim 1 wherein each dosage unit contains from more than 50 to 200 mg of the said 21-adamantane- 1'-carboxylate.

3. Compositions as defined in claim 1 adapted for parenteral administration.

4. Compositions as defined in claim 1 adapted for intramuscular administration.

5. Compositions as defined in claim 3 containing a sterile aqueous vehicle.

6. Compositions as defined in claim 5 in the form of ampoules or vials.

7. Compositions as defined in claim 1 wherein each dosage unit contains from more than 50 to 500 mg of betamethasone 21-adamantane- 1'-carboxylate.

8. Compositions as claimed in claim 1 wherein each dosage unit contains from more than 50 to 500 mg of dexamethasone 21-adamantane- 1'-carboxylate.

9. Compositions as claimed in claim 1 wherein each dosage unit contains from 60 to 150 mg of betamethasone 21-adamantane- 1'-carboxylate, dexamethasone 21-adamantane- 1'-carboxylate or a corresponding 11-ketone.

* * * * *